(12) United States Patent
Boppana et al.

(10) Patent No.: US 9,328,050 B1
(45) Date of Patent: May 3, 2016

(54) PROCESSES FOR MAKING HYDROXYMETHYLBENZOIC ACID COMPOUNDS

(71) Applicant: Eastman Chemical Company, Kingsport, TN (US)

(72) Inventors: Venkata Bharat Ram Boppana, Johnson City, TN (US); Robert Thomas Hembre, Johnson City, TN (US); Scott Donald Barnicki, Kingsport, TN (US); Shane Kipley Kirk, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/581,369

(22) Filed: Dec. 23, 2014

(51) Int. Cl.
    *C07C 51/347* (2006.01)
(52) U.S. Cl.
    CPC .................................. *C07C 51/347* (2013.01)
(58) Field of Classification Search
    None
    See application file for complete search history.

(56) References Cited

U.S. PATENT DOCUMENTS

| | | | |
|---|---|---|---|
| 2,109,844 A | 3/1938 | Lazier | |
| 2,139,369 A | 12/1938 | Kyrides | |
| 2,221,882 A | 11/1940 | Rosenberg | |
| 2,446,430 A | 8/1948 | Norton | |
| 2,675,390 A | 4/1954 | Rosenblatt | |
| 2,687,430 A | 8/1954 | Snow et al. | |
| 2,789,509 A | 4/1957 | Reynolds et al. | |
| 2,814,649 A | 11/1957 | Pritchard | |
| 2,828,335 A | 3/1958 | Ferstandig et al. | |
| 2,877,190 A | 3/1959 | Canterino | |
| 2,888,484 A | 5/1959 | Dehm et al. | |
| 2,939,886 A | 6/1960 | Prtichard et al. | |
| 3,162,679 A | 12/1964 | Rylander et al. | |
| 3,267,157 A | 8/1966 | Miya | |
| 3,326,972 A | 6/1967 | Schenk et al. | |
| 3,334,149 A | 8/1967 | Akin et al. | |
| 3,444,237 A | 5/1969 | Jaffe | |
| 3,520,921 A | 7/1970 | Appell | |
| 3,557,222 A | 1/1971 | Withers, Jr. et al. | |
| 3,560,429 A | 2/1971 | Bilow et al. | |
| 3,607,917 A | 9/1971 | Buls | |
| 3,993,699 A | 11/1976 | Maeda et al. | |
| 4,053,510 A | 10/1977 | Zengel et al. | |
| 4,149,021 A | 4/1979 | Wall | |
| 4,239,703 A | 12/1980 | Bernhardt et al. | |
| 4,283,565 A | 8/1981 | Bernhardt et al. | |
| 4,301,088 A | 11/1981 | Bernhardt | |
| 4,431,798 A | 2/1984 | Paschke et al. | |
| 4,448,987 A * | 5/1984 | Lillwitz | C07C 29/149 560/64 |
| 4,611,085 A | 9/1986 | Kitson | |
| 4,754,064 A | 6/1988 | Lillwitz | |
| 4,804,791 A | 2/1989 | Kitson et al. | |
| 4,837,367 A | 6/1989 | Gustafson et al. | |
| 4,837,368 A | 6/1989 | Gustafson et al. | |
| 4,929,777 A | 5/1990 | Irick, Jr. et al. | |
| 4,973,717 A | 11/1990 | Williams | |
| 5,118,841 A | 6/1992 | Cook et al. | |
| 5,202,475 A | 4/1993 | Cook et al. | |
| 5,278,339 A | 1/1994 | Cook | |
| 5,286,898 A | 2/1994 | Gustafson et al. | |
| 5,334,779 A | 8/1994 | Kuo | |
| 5,387,752 A | 2/1995 | Scarlett et al. | |
| 5,430,184 A | 7/1995 | Tateno et al. | |
| 5,763,353 A | 6/1998 | Kadono et al. | |
| 5,929,274 A | 7/1999 | Lamshing et al. | |
| 6,113,866 A | 9/2000 | Lee et al. | |
| 6,187,968 B1 | 2/2001 | Itoh et al. | |
| 6,284,932 B1 | 9/2001 | Fischer et al. | |
| 6,291,706 B1 | 9/2001 | Sumner, Jr. et al. | |
| 6,294,703 B1 | 9/2001 | Hara et al. | |
| 6,495,730 B1 | 12/2002 | Konishi et al. | |
| 6,600,080 B1 | 7/2003 | Nagamura et al. | |
| 6,797,844 B2 | 9/2004 | Nakai | |
| 6,919,489 B1 | 7/2005 | McCusker-Orth | |
| 7,615,671 B2 | 11/2009 | Puckette et al. | |
| 2005/0234269 A1 | 10/2005 | Kilner et al. | |
| 2010/0286287 A1 | 11/2010 | Walden | |
| 2012/0296111 A1 | 11/2012 | Königsmann et al. | |
| 2013/0029831 A1 | 1/2013 | Kilner et al. | |
| 2013/0030222 A1 | 1/2013 | Barton et al. | |
| 2015/0183699 A1 | 7/2015 | Hembre et al. | |
| 2015/0183706 A1 | 7/2015 | Hembre et al. | |

FOREIGN PATENT DOCUMENTS

| | | |
|---|---|---|
| CN | 1911885 A | 2/2007 |
| CN | 101812170 A | 8/2010 |
| EP | 0 225 802 A2 | 6/1987 |

(Continued)

OTHER PUBLICATIONS

Brindell, Gordon D. et al.; "Polymer Applications of Some Terephthalaldehyde Derivatives": Ind. Eng. Chem., Prod. Res. Dev., vol. 15, No. 1; 1976; pp. 83-88.

Harper, Jon Jay and Janik, Paul; "Terephthalic Acid Solubility"; Journal of Chemical and Engineering Data, vol. 15, No. 3; 1970; pp. 439-440.

Kibler, Charles J. et al.; "Polyesters of 1,4-Cyclohexanedimethanol"; Journal of Polymer Science: Part A, vol. 2; 1964; pp. 2115-2125.

Li, Dian-Qing et al.; "Solubilities of Terephthalaldehydic, p-Toluic, Benzoic, Terephthalic, and Isophthalic Acids in N-Methyl-2-pyrrolidone from 295.65 K to 371.35K"; Journal of Chemical Engineering Data, vol. 46; 2001; pp. 172-173.

(Continued)

*Primary Examiner* — Sudhakar Katakam
*Assistant Examiner* — Jennifer C Sawyer
(74) *Attorney, Agent, or Firm* — James Arnold, Jr.

(57) ABSTRACT

This invention relates to hydrogenation processes for making hydroxymethylbenzoic acid compounds. More specifically, this invention relates to hydrogenation processes in the presence of tertiary amide solvent compounds, as well as compositions that can result from such processes. The invention thus provides processes for making hydroxymethylbenzoic acid compounds.

20 Claims, No Drawings

(56) References Cited

FOREIGN PATENT DOCUMENTS

| EP | 0 523 818 B2 | 8/2000 |
|---|---|---|
| GB | 1 254 927 | 11/1971 |
| JP | 2001-181223 A | 7/2001 |
| JP | 2002-60356 A | 2/2002 |
| JP | 2002-69016 A | 3/2002 |
| JP | 2004-300130 A | 10/2004 |

OTHER PUBLICATIONS

Pinkus, A. G. and Hariharan, Rajan; Poly-3- and 4-hydroxymethlybenzoates: Future Engineering/Fiber "Plastics"?; Journ. Macro. Sci.—Rev. Macromol. Chem. Phys., C33(3); 1993; pp. 259-289.

Prasad, Ram and Singh, Pratichi; "Applications and Preparation Methods of Copper Chromite Catalysts: A Review"; Bulletin of Chemical Reaction Engineering & Catalysis, vol. 6, No. 2; 2011; pp. 63-113.

Satchell, D. P. N. and Satchell, R. S.; "Quantitative Aspects of the Lewis Acidity of Covalent Metal Halides and Their Organo Derivatives"; Chemical Reviews, vol. 69, No. 3; Jun. 1969; pp. 251-278.

Turner, S. Richard; "Development of Amorphous Copolyesters Based on 1,4-Cyclohexanedimethanol"; Journal of Polymer Science: Part A: Polymer Chemistry, vol. 42; 2004; pp. 5847-5852.

Twigg, Martyn V. and Spencer, Michael S.; "Deactivation of supported copper metal catalysts for hydrogenation reactions"; Applied Catalysis A: General, vol. 212; 2001; pp. 161-174.

Properties & Uses for Terephthalic Acid, Sevas Educational Society retrieved from http://www.sbioinformatics.com/design_thesis/Terephthalic_acid/Terephthalic-2520acid_Properties&uses.pdf, Accessed Dec. 7, 2012.

Notification of Transmittal of the International Search Report and the Written Opinion of the International Searching Authority, or the Declaration date of mailing Mar. 23, 2015 received in corresponding International Patent Application No. PCT/US2014/070731.

Notification of Transmittal of the International Search Report and the Written Opinion of the International Searching Authority, or the Declaration date of mailing Mar. 30, 2015 received in corresponding International Patent Application No. PCT/US2014/070733.

\* cited by examiner

PROCESSES FOR MAKING HYDROXYMETHYLBENZOIC ACID COMPOUNDS

FIELD OF THE INVENTION

This invention relates to hydrogenation processes for making hydroxymethylbenzoic acid compounds. More specifically, this invention relates to hydrogenation processes in the presence of tertiary amide solvent compounds, as well as compositions that can result from such processes.

BACKGROUND OF THE INVENTION

Hydroxymethylbenzoic acid compounds are important commercial chemicals. For example, compounds such as 4-hydroxylmethyl benzoic acid (4-HMBA) and 3-hydroxylmethyl benzoic acid (3-HMBA) are useful monomers in formation of polymers and intermediates in a variety of additional reactions. While several methods for making such compounds are known, many such routes do not achieve desirable raw material conversion rates and high selectivity for the intended product. Some processes require formation of an intermediate, requiring two reaction steps. There is a continuing need to find a manufacturing method that involves a single step and achieves favorable selectivity and conversion rates.

BRIEF SUMMARY OF THE INVENTION

The invention provides for making a hydroxymethylbenzoic acid compound comprising combining hydrogen, a benzene dicarboxylic acid compound and a solvent in the presence of an acid hydrogenation catalyst in a reaction zone to form a product composition comprising a hydroxymethylbenzoic acid compound, wherein the solvent comprises a tertiary cyclic amide solvent compound.

In some embodiments of the process, the tertiary cyclic amide solvent compound has the structure depicted in formula I or II:

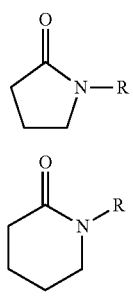

wherein R is selected from alkyl, cycloalkyl, aryl, aryl-substituted alkyl, cycloalkyl-substituted alkyl, alkyl-substituted aryl and alkyl-substituted cycloalkyl, and wherein R has from 1 to 10 carbon atoms and optionally possesses one hydroxyl group. In some embodiments R is an unsubstituted alkyl group. In some embodiments, R is methyl or ethyl. In some embodiments, R is 2-hydroxyethyl. In some embodiments, the tertiary amide solvent compound has the structure depicted in Formula I with R having one or two carbon atoms. In embodiments of each of the processes and embodiments described above, at least about 50% by weight of the solvent is a tertiary cyclic amide solvent compound.

In some embodiments of each of the processes and embodiments described above, the diacid is terephthalic acid.

In some embodiments of each of the processes and embodiments described above, the acid hydrogenation catalyst comprises (a) a ruthenium compound; and (b) a tridentate triphosphine compound selected from 1,1,1-tris(diarylphosphinomethyl)alkyl in which the alkyl is substituted or unsubstituted.

In some embodiments of each of the processes and embodiments described above, the diacid is terephthalic acid.

In some embodiments of each of the processes and embodiments described above, the acid hydrogenation catalyst comprises: (a) a ruthenium compound; and (b) a tridentate triphosphine compound selected from 1,1,1-tris(diarylphosphinomethyl)alkyl in which the alkyl is substituted or unsubstituted. In some embodiments of each of the processes and embodiments described above, the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes and combinations of two or more of the foregoing; and the tridentate triphosphine compound is selected from tris(diphenylphosphinomethyl)alkyl or substituted alkyl. Further, in some embodiments of each of the processes and embodiments described above, the ruthenium compound and the tridentate triphosphine compound are the same compound. For example, in some embodiments the tridentate triphosphine compound comprises 1,1,1-tris(diphenylphosphinomethyl)ethane.

In some embodiments of each of the processes and embodiments described above, the process further comprises feeding to the second reaction zone a promoter selected from Lewis acids, protic acids having an ionization constant ($K_i$) of $5 \times 10^{-3}$ or greater, onium salts, and combinations of two or more of the foregoing. In some embodiments of each of the processes and embodiments described above, the promoter is selected from ammonium hexafluorophosphate, tetrabutylammonium hexafluorophosphate, tetraphenylphosphonium bromide, sodium tetraphenyl borate, ammonium tetrafluoroborate, tetramethyl ammonium tetrafluoroborate, toluenesulfonic acid, phosphoric acid, triflic acid, sulfuric acid, methanesulfonic acid, trifluoroacetic acid, dodecylbenzenesulfonic acid, dinonylnaphthalenesulfonic acid, and combinations of two or more of the foregoing. In some embodiments of each of the processes and embodiments described above, the promoter is selected from tetrabutylammonium hexafluorophosphate, triflic acid, toluenesulfonic acid, dodecylbenzenesulfonic acid, dinonylnaphthalenesulfonic acid, and combinations of two or more of the foregoing.

In some embodiments of each of the processes and embodiments described above, the reaction zone has a pressure of from about 500 to about 3,000 psig and a temperature of from about 100 to about 240° C.

In some embodiments of each of the processes and embodiments described above, the process further comprises processing at least some of the product composition in a first separation zone to remove at least some of the acid hydrogenation catalyst from the product composition. In such embodiments the process can optionally further comprise processing at least some of the product composition in a second separation zone to concentrate the hydroxymethylbenzoic acid in a crude product stream and to concentrate the solvent compound in a recovered solvent stream. In such embodiments the process can optionally further comprise recycling at least some of the recovered solvent stream to the reaction zone.

DETAILED DESCRIPTION

The invention provides processes that include hydrogenation of benzene dicarboxylic acids in the presence of a tertiary cyclic amide solvent compound to form hydroxymethylbenzoic acid compounds.

Solvents and Tertiary Cyclic Amide Solvent Compounds

The solvent in the hydrogenation process includes a tertiary cyclic amide solvent compound. As used throughout this application, "cyclic amide solvent compounds" or "cyclic amide compounds" refers to cyclic compounds (commonly referred to as lactam compounds) containing an amide group in which both the nitrogen of the amide group and the carbon of the carbonyl moiety of the amide group are members of the cyclic rings. Some examples include four membered rings based on β-lactam (2-azetidinone), five membered rings based on γ-lactam (2-pyrrolidone), six membered rings based on δ-lactam (2-piperidone) and seven membered rings based on ε-lactam (azepan-2-one or caprolactam) compounds. The cyclic amide solvent compounds of the present invention are tertiary cyclic amides, meaning that the nitrogen atom in the amide is bonded to three carbon atoms. Two of the carbon atoms are members of the ring, and the third carbon is part of a group referred to as "R," herein. For example, tertiary amides based on 2-pyrrolidone and 2-piperidone have the structure shown in formula I and II:

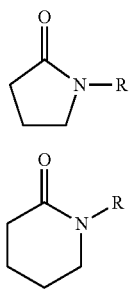

Although 2-pyrrolidone and 2-piperidone are used as illustrations above, embodiments exist in which other tertiary cyclic amide solvent compounds are used, and the descriptions of the R group herein can apply to the corresponding group on any tertiary cyclic amide. As used throughout this application, "tertiary cyclic amide solvent compounds" refers to all such compounds. In some embodiments, the tertiary cyclic amide solvent compound is selected from compounds having the structure shown in formula I or II or combinations of two or more thereof. In some embodiments, the tertiary cyclic amide solvent compound is selected from compounds having the structure shown in formula I or combinations of two or more thereof. In some embodiments, the tertiary cyclic amide solvent compound is selected from compounds having the structure shown in formula II or combinations of two or more thereof.

The R group in the tertiary cyclic amide solvent compound is selected from substituted or unsubstituted alkyl, cycloalkyl, aryl, aryl-substituted alkyl, cycloalkyl-substituted alkyl, alkyl-substituted aryl, and alkyl-substituted cycloalkyl, and wherein R has 1 to 10 carbon atoms and optionally possesses one or more hydroxyl (—OH) groups. In some embodiments, the R group possesses a single terminal hydroxyl group (i.e. a hydroxyl group bonded to a carbon that is furthest from the nitrogen). Embodiments exist in which R is an alkyl having 1 to 10 carbon atoms, 1 to 6 carbon atoms, 1 to 4 carbon atoms, 1 to 3 carbon atoms or 1 to 2 carbon atoms, each of the foregoing having embodiments that possess a terminal hydroxyl groups and embodiments that do not. Embodiments of each of these exist in which the alkyl group includes a hydroxyl group or where it does not. Some examples of alkyl groups suitable for R include methyl, ethyl, n-propyl, isopropyl, n-butyl, isobutyl, tert-butyl, n-pentyl, n-hexyl, n-heptyl, n-octyl, and 2-hydroxyethyl. In some embodiments, R is selected from methyl and ethyl. In some embodiments, R is selected from methyl, ethyl, and 2-hydroxyethyl. In some embodiments, R is methyl (e.g. n-methyl-2-pyrrolidone or n-methyl-2-piperidone). In some embodiments, R is ethyl (e.g. n-ethyl-2-pyrrolidone or n-ethyl-2-piperidone). In some embodiments, R is 2-hydroxyethyl (e.g. n-2-hydroxyethyl-2-pyrrolidone or n-2-hydroxyethyl-2-piperidone). Combinations of two or more compounds of the foregoing description may also be used, including combinations of compounds having differing R groups.

In some embodiments, the tertiary cyclic amide solvent compound constitute(s) at least about 50% of the solvent. In some embodiments, the tertiary cyclic amide solvent compound constitute(s) at least about 75% of the solvent. In some embodiments, the tertiary cyclic amide solvent compound constitute(s) at least about 85% of the solvent. In some embodiments, the tertiary cyclic amide solvent compound constitute(s) at least about 90% of the solvent. In some embodiments, the tertiary cyclic amide solvent compound constitute(s) at least about 95% of the solvent. A tertiary cyclic amide solvent compound may be used alone, in blends of two or more tertiary cyclic amide solvent compounds, in blends with any other types of solvent compounds, or both. Where other compounds are used in the solvent, any compound that does not unacceptably interfere with the hydrogenation reaction or the resulting selectivity can be used. The solvent compounds are part of the feed to a hydrogenation process and are present in an amount effective to provide adequate dissolution or suspension of the feed materials. In some embodiments, the solvent compounds together (i.e. the one or more tertiary cyclic amide solvent compounds and any other solvent compounds) is at least about 50 wt. % of the feed to the hydrogenation process. Embodiments also exist in which the solvent compounds are at least about 75 wt. %, at least about 80 wt. % or at least about 90 wt. % of the feed to the hydrogenation process.

Hydrogenation of Benzenedicarboxylic Acids

The process includes combining a benzenedicarboxylic acid compound, a solvent and hydrogen in the presence of an acid hydrogenation catalyst wherein the solvent has the characteristics described above. As used throughout this application, "benzene dicarboxylic acid" means a compound containing a six carbon aromatic ring or "benzene ring" in which two of the carbons in the ring are covalently bonded to the carbon of a carboxylic acid group. Some examples of benzene dicarboxylic acids include benzene-1,4-dicarboxylic acid (terephthalic acid), benzene-1,3-dicarboxylic acid (isophthalic acid) and benzene-1,2-dicarboxylic acid (phthalic acid). In some embodiments, the benzene dicarboxylic acid is selected from terephthalic acid, isophthalic acid or combinations thereof. In some embodiments, the benzene dicarboxylic acid is terephthalic acid. In some embodiments, the benzene dicarboxylic acid is isophthalic acid. In some embodiments, the benzene dicarboxylic acid is a blend of terephthalic acid and isophthalic acid. Specific embodiments of the process exist for each of the foregoing, and embodiments exist for blends of any of the foregoing.

The benzene dicarboxylic acid and solvent may be fed to the hydrogenation process by any workable means (i.e.

together or separately as workable). In some embodiments, the benzene dicarboxylic acid is dissolved or dispersed in the solvent and the two are fed together. Any workable concentration of the benzene dicarboxylic acid in solvent may be used. In some embodiments, the mixture contains from about 5 to about 60 wt. % benzene dicarboxylic acid. In some embodiments, the amount is from about 5 to about 10.%, from about 5 to about 15 wt. %, from about 5 to about 20 wt. %, from about 5 to about 40 wt. %, from about 10 to about 20 wt. %, from about 10 to about 30 wt. %, from about 20 to about 40 wt. %, from about 10 to about 50 wt. %, from about 30 to about 40 wt. %, from about 10 to about 30 wt. %, from about 20 to about 60 wt. %, from about 20 to about 50 wt. %.

The process may be operated at any weight hour space velocity that is useful to the process. Weight hour space velocity is the ratio of mass feed rate for TPA (unit weight per hour) to mass of catalyst (including support). In some embodiments, the weight hour space velocity is from about 0.1 to about 3.0. Embodiments also exist in which the weight hour space velocity is from about 0.1 to about 2.0, from about, 0.5 to about 2.0, or from about 0.75 to about 1.5, from about 0.1 to about 1.0, or from about 0.1 to about 0.5.

The acid hydrogenation catalyst may be any hydrogenation catalyst that is effective for the reduction of one of the two carboxylic acid groups on the benzene dicarboxylic acid to a hydroxymethyl group (i.e. $CH_2OH$). In some embodiments, the acid hydrogenation catalyst is a homogeneous catalyst that is dissolved or dispersed in the solvent. In some embodiments, the catalyst composition includes: (a) a ruthenium, rhodium, iron, osmium or palladium compound; and (b) an organic phosphine. In some embodiments, the catalyst of the present invention is a ruthenium catalyst. The ruthenium compound is not particularly limiting and can be any ruthenium source that is soluble in the solvent of the invention. Some example compounds include ruthenium salts, hydride complexes, carbonyl compounds, halides, oxides, phosphine complexes, and combinations of two or more of the foregoing. Suitable ruthenium salts include ruthenium carboxylates and acetylacetonates. For example, the ruthenium compound can include the acetonylacetonate complex of ruthenium(III). In some embodiments, the ruthenium compounds can be converted to active species under the reaction conditions, such as nitrates, sulfates, carboxylates, beta diketones, and carbonyls. Ruthenium oxide, carbonyl ruthenates and complex compounds of ruthenium, including hydridophosphineruthenium complexes, may also be used. Some examples include ruthenium nitrate, ruthenium dioxide, ruthenium tetroxide, ruthenium dihydroxide, ruthenium acetylacetonate, ruthenium acetate, ruthenium maleate, ruthenium succinate, tris-(acetylacetone)ruthenium, triruthenium dodecacarbonyl, tetrahydrido(decacarbonyl)tetraruthenium, hydrido(undecacarbonyl)triruthenate cyclo-pentadienyl(dicarbonyl)ruthenium dimer, (norbornadiene)bis(methallyl)ruthenium, (cyclooctadiene)bis(methallyl)ruthenium, bis(ethylene)bis(methallyl)ruthenium, ruthenium dioxide, ruthenium tetraoxide, ruthenium dihydroxide and bis(tri-n-butylphosphine)tricarbonylruthenium.

In some embodiments, the ruthenium compound is a tridentate phosphine. Some examples of tridentate phosphine compounds include tris-1,1,1-(diphenylphosphinomethyl)methane, tris-1,1,1-(diphenylphosphinomethyl)ethane, tris-1,1,1-(diphenylphosphinomethyl)propane, tris-1,1,1-(diphenylphosphino-methyl)butane, tris-1,1,1-(diphenylphosphinomethyl)2,2dimethylpropane, tris-1,3,5-(diphenylphosphinomethyl)cyclohexane, tris-1,1,1-(dicyclohexylphosphinomethyl)ethane, tris-1,1,1-(dimethylphosphinomethyl)ethane, tris-1,1,1-diethylphosphinomethyl)ethane, tris-1,1,1-(dimethylphospholylmethyl)ethane, 1,5,9-triethyl-1,5-9-triphosphacyclododecane, 1,5,9-triphenyl-1,5-9-triphosphacyclododecane, tris(2-diphenylphosphinoethyl)amine, and tris (diisopropylphosphinomethyl)amine. In some embodiments, tris-1,1,1-(diphenylphosphinomethyl)-ethane is used. Advantageous results can be achieved with tridentate facially capped phosphines such as tris-1,1,1-(diarylphosphinomethyl)alkane and tris-1,1,1-(dialkylphosphinomethyl)alkane.

In some embodiments, the catalyst composition includes: (a) a ruthenium compound; (b) a tridentate triphosphine compound selected from 1,1,1-tris(diarylphosphinomethyl)alkyl or substituted alkyl; and (c) a promoter selected from Lewis acids, protic acids having an ionization constant (K) of $5 \times 10^{-3}$ or greater, onium salts, and combinations of two or more of the foregoing; wherein the catalyst components. In some embodiments, (a) and (b) are the same compound.

In some embodiments, the tridentate triphosphine is selected from 1,1,1-tris(diarylphosphinomethyl)alkyl and substituted alkyl. The alkyl substituent can have 1 to 40 carbon atoms. Some examples of alkyl groups include methyl, ethyl, propyl, butyl, pentyl, isobutyl, isopropyl, isopentyl, and the like. The alkyl group can be substituted with any group that does not interfere with the hydrogenation reaction such as, for example, hydroxyl, ether, halogen, sulfonic acid, carboxylic acid, and the like. The aryl group of the tridentate triphosphine compound may have from 6 to 20 carbon atoms. Some examples of the aryl groups include carbocyclic aryl groups such as phenyl, naphthyl, anthracenyl, and substituted derivatives thereof in which one or more substituent groups can replace hydrogen at any carbon position on the aromatic ring(s). Some examples of substituent groups include one or more groups selected from alkyl, alkoxy, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms.

Some representative examples of substituted aryl groups include 2-fluorophenyl, 2,3,4,5,6-pentafluorophenyl, 3,5-bis(trifluoromethyl)phenyl and the like; a mono- or di(hydroxy) aryl radical such as 4-hydroxyphenyl, 3-hydroxyphenyl, 2,4-dihydroxyphenyl, and the like; for example, 4-cyanophenyl; a mono- or di(lower alkyl)aryl radical such as 4-methylphenyl, 2,4-dimethylphenyl, 2-methylnaphthyl, 4-(isopropyl)phenyl, 4-ethylnaphthyl, 3-(n-propyl)phenyl and the like; a mono- or di(alkoxy)aryl radical, for example, 2,6-dimethoxyphenyl, 4-methoxyphenyl, 3-ethoxyindenyl, 4-(isopropoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl)aryl radical such as 2-(aminomethyl)phenyl, or a mono- or di(methylsulfonylamino)aryl radical such as 3-(methylsulfonylamino)naphthyl. In some embodiments, for example, tridentate triphosphine compound can be selected from 1,1,1-tris(diphenylphosphinomethyl)alkyl and substituted alkyl. In some embodiments, the ruthenium compound can be selected from ruthenium salts, hydride complexes, carbonyl compounds, halides, oxides, phosphine complexes, and combinations of two or more of the foregoing; and the tridentate triphosphine compound can be selected from 1,1,1-tris(diphenylphosphinomethyl)alkyl and substituted alkyl. In some embodiments, the tridentate triphosphine is 1,1,1-tris (diphenylphosphinomethyl)ethane (also known as TRIPHOS).

Optionally, the rate of reaction can be enhanced by the addition of a promoter selected from Lewis acids, protic acids having an ionization constant (K) of $5 \times 10^{-3}$ or greater, and onium salts. The term "Lewis Acid", as used herein, refers to the Lewis concept of acid-base equilibria as elaborated in Chemical Reviews, 69, 251 (1969). One example of a Lewis acid promoter is zinc acetonylacetonate.

Where used, onium salt promoters can include an anionic component that is derived from a strong acid having an ionization constant (K) of $5 \times 10^{-3}$ or greater such as, for example, phosphoric acid, hexafluorophoshoric acid, hydrobromic acid, tetrafluoroboric acid, trifluoroacetic acid, p-toluenesulfonic acid, triflic acid, sulfuric acid, combinations of two or more of the foregoing, and the like. These anions are neutral to weak bases in comparison to anions such as, for example, hydroxides, carbonates, bicarbonates, and carboxylates without electron-withdrawing substituents. In some embodiments, the onium salt promoters can include a non-coordinating anion. Some examples of onium salt promoters include ammonium hexafluorophosphate, tetrabutylammonium hexafluorophosphate, tetraphenylphosphonium bromide, ammonium tetrafluoroborate, tetramethyl ammonium tetrafluoroborate, combinations of two or more of the foregoing and the like.

Some examples of protic acids having an ionization constant $(K_i)$ of $5 \times 10^{-3}$ or greater include toluenesulfonic acid, phosphoric acid, triflic acid, sulfuric acid, methanesulfonic acid, trifluoroacetic acid, dodecylbenzenesulfonic acid, dinonylnaphthalenesulfonic acid, and the like. In some embodiments, the promoter is selected from tetrabutylammonium hexafluorophosphate, triflic acid, toluenesulfonic acid, dodecylbenzenesulfonic acid, dinonylnaphthalenesulfonic acid, and combinations of two or more of the foregoing. Combinations of any one of the above Lewis acids, protic acids, and onium salts also may be used.

The benzene dicarboxylic acid compound, solvent and hydrogen are combined in the presence of the acid hydrogenation catalyst (and optional promoter) under conditions effective to cause hydrogenation of the carboxylic acid groups. In some embodiments, the pressure in the reactor is from about 500 to about 5,000 psig and the temperature in the reactor is from about 100° C. to about 250° C. In some embodiments the temperature is from about 150° C. to about 225° C. In some embodiments the temperature is from about 100° C. to about 200° C. In some embodiments the temperature is from about 100° C. to about 150° C. In some embodiments the temperature is from about 160° C. to about 210° C. In some embodiments the pressure is from about 1200 psig to about 3000 psig, in some embodiments the pressure is from about 1000 psig to about 6000 psig, in some embodiments the pressure is from about 500 psig to about 3000 psig, in some embodiments the pressure is from about 1000 psig to about 2500 psig, in some embodiments the pressure is from about 1000 psig to about 2500 psig, in some embodiments the pressure is from about 1000 psig to about 2000 psig, in some embodiments the pressure is from about 1500 psig to about 2000 psig, in some embodiments the pressure is from about 1400 psig to about 2000 psig and in some embodiments from about 1400 to about 1600 psig. Combinations of any of the above temperature and pressure ranges are within the scope of the invention.

The hydrogenation of benzene dicarboxylic acids of the present invention be conducted under continuous, semi-continuous, and batch modes of operation and can utilize a variety of reactor types. By "continuous" it is meant that the process is substantially or completely continuous in operation and is to be contrasted with a "batch" process. "Continuous" is not meant in any way to prohibit normal interruptions in the continuity of the process due to, for example, start-up, equipment maintenance, or scheduled shut down periods. The term "batch" process as used herein means a process wherein all the reactants are added to the reaction zone and then processed according to a predetermined course of reaction during which no material is fed or removed into the reactor. The term "semicontinuous" means a process where some of the reactants are charged at the beginning of the process and the remaining reactants are fed continuously as the reaction progresses to completion. Alternatively, a semicontinuous process may also include a process similar to a batch process in which all the reactants are added at the beginning of the process except that one or more of the products are removed continuously as the reaction progresses.

Any effective reactor designs or configurations may be used in carrying out the process of the present invention. Some examples of suitable reactor types include stirred tank, continuous stirred tank, tower, plug flow reactor, radial flow reactor, bubble column, heated tube type reactor and tubular reactor. The process also may be practiced in a batchwise manner by contacting the low molecular weight alcohol, hydrogen and carbon monoxide with the present catalyst composition in an autoclave. Thus, in some embodiments, the reaction zone is selected from one of the foregoing reactor types. Embodiments exist of each such type.

In some embodiments, the duration or contact of the benzene dicarboxylic acid with the hydrogen and the acid hydrogenation catalyst is from about 0.25 to about 10.0 hours, in some embodiments from about 1.0 to about 6.0 hours, in some embodiments from about 1.0 to about 3.0 hours, in some embodiments from about 2.0 to about 4.0 hours, in some embodiments from about 0.1 hour to about 2.0 hours, in some embodiments from about 0.1 hour to about 1.0 hour, in some embodiments from about 0.2 hour to about 0.8 hour, in some embodiments about 0.5 to about 20 hours, in some embodiments from about 1 to about 15 hours and in some embodiments from about 4 to about 12 hours.

In some embodiments, the duration or contact of the benzene dicarboxylic acid with the hydrogen and the acid hydrogenation catalyst is from about 0.5 to about 20 hours, in some embodiments from about 2 to about 15 hours and in some embodiments from about 4 to about 12 hours. In some embodiments, the weight hour space velocity is from about 0.1 to about 3.0. Embodiments also exist in which the weight hour space velocity is from about 0.5 to about 2.0, or from about 0.75 to about 1.5.

Additional Process Steps

The process can further involve using separation zones or separation processes to provide a product stream having a desired composition. For example, where a dissolved or other homogeneous acid hydrogenation catalyst is used, separation techniques may be used to separate the product and solvent from the catalyst. Any useful separation technique can be used. Some examples include vapor stripping, flash distillation, liquid-liquid extraction and membrane separation. For example, DURAMEM 150 and 280 membranes available from Evonik Industries AG (Essen, Germany) have been observed to be effective to separate Ruthenium TRIPHOS catalyst from liquid compositions containing cyclohexane compounds when used, for example, in stirred cell filters such as those available from Sterlitech Corporation. The catalyst, once separated from the product, can optionally be returned to a reaction zone or process for reuse. Alternatively, the catalyst solution can be diluted with another acceptable solvent reused. As another alternative, the reaction mixture can be partitioned between an aqueous phase and an organic phase, which will dissolve the catalyst components. The hydroxymethylbenzoic acid compound product can then be recovered from the aqueous phase by simple distillation while the organic phase can be returned to the reactor for reuse. It is understood that the separation process described above can be combined with any of the various embodiments of the inventive process described herein.

The process may also include processes or zones to separate one or more resulting product stream from at least some of the solvent and to further purify the product stream. For example, a separation process can concentrate the product hydroxymethylbenzoic acid in a product stream and concentrate solvent into a recovered solvent stream. By "concentrating" a product compound, it is meant that the weight percent of product compound present in product stream is higher than that in the stream fed to the separation process or zone. Similarly, by "concentrating" a solvent compound, it is meant that the weight percent of solvent compound present in a recovered solvent stream is higher than that in the stream fed to the separation process or zone. Any useful separation zone or process can be used. Some examples of separation processes that may be used in some embodiments include distillation, filtration, crystallization and extraction and combinations thereof. Some examples of separation zones that can be used include vessels or equipment that can perform any of the foregoing processes. Recovered solvent may be optionally recycled for reuse in the process. Additional product refining and purification may occur (for example, through another separation process or zone), or separation into more than two streams can be achieved in a single process. In embodiments in which catalyst materials are also separated from one or more streams, the solvent separation can occur before, during or after a catalyst separation process. In some embodiments, catalyst is separated from the product stream in a first separation zone and solvent is separated from the product stream in a second separation zone. In some embodiments, the order is reversed. In some embodiments, catalyst and solvent is separated from the product stream in a single separation zone. In some embodiments, one or more of the foregoing separation zones further serves to separate additional materials.

Product streams may be processed further to obtain desired final compositions. Thus, for example, products may be processed further in one or more additional separation zones of any of the types described above.

Resulting Compositions

The invention further provides compositions that contain a hydroxymethylbenzoic acid compound of the type described above and a cyclic amide solvent compound of the type described above. Any combination of the two described above may be in the composition including all compositions that can result from the processes described herein. Thus, in some embodiments, the composition includes any combination of one or more additional solvent compounds of the type described above. Again, combination of the two described above may be in the composition including all compositions that can result from the processes described herein and, in some embodiments, the composition includes any combination of one or more additional solvent compounds of the type described above.

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims. Unless otherwise indicated, all percentages are by weight.

EXAMPLES

Except as otherwise stated in the individual examples, the following procedures were used for hydrogenation of terephthalic acid to 4-hydroxymethylbenzoic acid (HMBA). A 100 ml autoclave configured in a high pressure AUTO-MATE System Model 4590 (H.E.L. Inc., Grand Rapids, Mich.). At atmospheric conditions, 0.25 grams of the catalyst Ruthenium 1,1,1-tris(diphenylphosphinomethyl)ethane (Ruthenium TRIPHOS), 2.0 grams reactant terephthalic acid and 0.02 grams p-toluene sulfonic acid (PTSA) and 30 grams of solvent were added to the autoclave. The reactor was then pressurized to 1500 psig with nitrogen. Nitrogen was slowly vented. The reactor was then purged two more times by pressurizing with nitrogen to 200 psig, then venting the pressure to atmospheric each time. The manifold to the reactor was then purged twice with hydrogen gas (atmospheric pressure). The reactor was then purged three times by pressurizing with hydrogen to approximately 300 psig, then venting the pressure to atmospheric each time. Agitation at 1000 rpm was then commenced, and hydrogen was then added to bring the pressure to 750 psig. The temperature was then increased to 190° C. while allowing pressure to rise. After passing 185° C., hydrogen pressure was increased to 1500 psig. These conditions (190° C. and 1500 psig) were held for 10 hours of reaction. After 10 hours of reaction, the agitation was stopped and the heat turned off to let the autoclave start cooling. After cooling to room temperature, pressure was released and the contents were twice pressurized with nitrogen gas and vented. The solution was finally discharged from the autoclave and analyzed by GC, and, in some cases, by gas chromatography—mass spectrometry (GC-MS).

The autoclave was then pressurized to 1500 psig with nitrogen. Nitrogen was slowly vented then the feed manifold to the reactor was then purged twice with by passing hydrogen gas through at atmospheric temperature. To activate the catalyst, the reactor was then purged three times by pressurizing with hydrogen to 150 psig, then venting to ambient pressure each time. Agitation at 450 rpm commenced and the reactor was heated to 150° C. Hydrogen was then added to bring the pressure to 1500 psig then held for 2 hours. The reactor was permitted to cool to room temperature, agitation was stopped and pressure was released. The reactor was then placed in a containment box purged with argon to avoid exposing the autoclave to air during loading. TPA (except where indicated otherwise), 3 g, and 50 grams of solvent (except where indicated otherwise) were charged to the autoclave. The agitator was then restarted and held at 450 rpm for 10 minutes. Nitrogen was slowly vented then the feed manifold to the reactor was then purged twice with hydrogen gas at atmospheric pressure. To the reactor was again purged three times by pressurizing with hydrogen to 150 psig, then venting the pressure then venting to ambient pressure each time. The autoclave was then heated to 140° C., the stirrer speed was increased to 800 rpm and the solution was held under these conditions for 40-50 minutes. After this, the catalyst basket was dropped in and hydrogen was then added to bring the pressure to 1500 psig then held for 4 hours. After 4 hours of reaction, hydrogen feed was discontinued and the autoclave was cooled to room temperature. Agitation was then stopped, pressure released, and the contents removed. The contents of the final product solution were filtered using vacuum filtration to remove any granules of the supported catalyst.

All references to NMP in the Examples are references to 99.5% anhydrous N-methyl-2-pyrrolidone (Sigma Aldrich). Except where indicated otherwise, all references to TPA are references to 98% terephthalic acid (Sigma Aldrich)

Analytical Procedures

All GC data in these examples were measured using the following procedures. A liquid sample of 0.03 g was dissolved in pyridine (200 µl), then reacted with N—O-bis(trimethylsilyl)trifluoroacetamide (BSTFA) at 80° C. for 30 minutes to ensure quantitative derivatization into corresponding trimethylsilyl derivatives. Separation and quantification was done with a GC column and a flame ionization detector (FID). The GC method used a DB-5 capillary column or equivalent (30 meters×0.32 mm ID×0.25 um film thickness), a split injector (at 330° C.), a flame ionization detector (at 300° C.), helium carrier gas at a constant linear velocity of 20.4 cm/sec (a Shimadzu GC 2010 or equivalent) or at an initial column head pressure of 5.7 psig, an oven temperature program of 40° C. initial temperature for 6 min, and 15° C./min temperature ramp to 300° C. for 6.66 min final hold time. A 1-ul sample of this solution was injected with a split ratio of 40:1. The method provided quantification range of 0.01-100 wt. % for each analyte within its separation capability.

Conversion percentages for TPA represent (moles of TPA converted divided by initial moles of TPA) multiplied by 100. Moles converted are determined by measuring the difference between the number of starting moles and the number of moles at completion. Selectivity percentages for the product 4-hydroxymethylbenzoic acid (4-HMBA) represent (the final moles of 4-HMBA divided by the total number of moles of TPA converted) multiplied by 100.

Mass balances in each example is (the final weight of the solution divided by the initial weight of the solution) multiplied by 100.

Examples 1-8

TPA Hydrogenation to 4-HMBA in NMP as a Solvent

The above procedure was followed using n-methyl pyrrolidone (NMP) as a solvent. Results are presented in Table I below. Example 7 was a repeat of Example 2 and Example 8 was a repeat of Example 6. Any variations from the procedure are also shown in Table I. After 4-HMBA, the highest concentration observed was the byproduct 1,4-xylylene glycol

TABLE 1

TPA hydrogenation to CHDA in the presence of NMP as a solvent.

| Example | T °C. | Time Hrs | TPA Wt. g | TPA Conv. % | HMBA Sel. % |
|---|---|---|---|---|---|
| 1 | 190 | 6 | 2 | 28.7 | 96.5 |
| 2 | 190 | 10 | 2 | 40.1 | 94.1 |
| 3 | 190 | 20 | 2 | 64.6 | 88.6 |
| 4 | 190 | 10 | 4 | 19.3 | 97.3 |
| 5 | 210 | 10 | 2 | 90.1 | 68.8 |

TABLE 1-continued

TPA hydrogenation to CHDA in the presence of NMP as a solvent.

| Example | T °C. | Time Hrs | TPA Wt. g | TPA Conv. % | HMBA Sel. % |
|---|---|---|---|---|---|
| 6 | 210 | 6 | 2 | 68.5 | 86.8 |
| 7 | 190 | 10 | 2 | 40.6 | 94.6 |
| 8 | 210 | 6 | 2 | 70.1 | 86 |

The results shown in Table 1 suggest that NMP is a suitable solvent for highly selective production 4-HMBA from TPA. Examples 3, 6 and 8 demonstrate favorable conversation and selectivity at 210 degrees C. GC-MS was conducted for Example 2. Qualitative analysis of GC-MS area %, it can be determined indicated TPA conversion of 42.6% and 4-HMBA selectivity of 91.7, confirming the analytical data.

Comparative Example C9

DMSO

The procedures of Example 2 were repeated using Dimethyl sulfoxide (DMSO) rather than NMP. Results (along with published solubility data, presented in grams of TPA per grams of solvent at 25° C.) are provided in Table 2. C10 is a repeat of C9. The data indicates that NMP confers a benefit beyond simply solubility.

TABLE 2

TPA hydrogenation to 4-HMBA in the presence of DMSO and NMP.

| Example | Solvent | Published TPA Solubility In Solvent g/100 g at 25° C. | TPA Conversion % | 4-HMBA Selectivity % |
|---|---|---|---|---|
| 2 | NMP | 5.5$^a$ ~5$^b$ | 40.1 | 94.1 |
| C9 | Dimethyl sulfoxide (DMSO) | 20$^c$ | Less than 0.1% | Less than 0.1% |
| C10 | Dimethyl sulfoxide (DMSO) | | Less than 0.1% | Less than 0.1% |

$^a$Li, D.Q., et al., "Solubilities of Terephthalaldehydic, p-Toluic, Benzoic, Terephthalic, and Isophthalic Acids in N-Methyl-2-pyrrolidone from 295.65K to 371.35K". Chem Eng. Data 46. 172. (2001).
$^b$U.S. Pat. No. 6,113,866
$^c$Published data contained in catalog of design theses at http://www.sbioinformatics.com/design_thesis/Terephthalic_acid/Terephthalic-2520acid_Properties&uses.pdf These data demonstrate that use of even a solvent having higher published solubility than that of NMP resulted in lower yields of CHDA and in some cases, no evidence of catalytic hydrogenation activity was observed.

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for making a hydroxymethylbenzoic acid compound comprising combining hydrogen, a benzene dicarboxylic acid compound and a solvent in the presence of an acid hydrogenation catalyst in a reaction zone to form a product composition comprising a hydroxymethylbenzoic acid compound, wherein the solvent comprises a tertiary cyclic amide solvent compound.

2. The process of claim 1, wherein the tertiary cyclic amide solvent compound has the structure depicted in formula I or II:

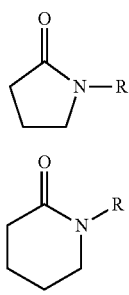

wherein R is selected from alkyl, cycloalkyl, aryl, aryl-substituted alkyl, cycloalkyl-substituted alkyl, alkyl-substituted aryl, and alkyl-substituted cycloalkyl, and wherein R has from 1 to 10 carbon atoms and optionally possesses one hydroxyl group.

3. The process of claim 2, wherein R is an unsubstituted alkyl group.

4. The process of claim 2, wherein R is methyl or ethyl.

5. The process of claim 2, wherein R is 2-hydroxyethyl.

6. The process of claim 2, wherein the tertiary amide solvent compound has the structure depicted in Formula I with R having one or two carbon atoms.

7. The process of claim 2, wherein at least about 50% by weight of the solvent is a tertiary cyclic amide solvent compound.

8. The process of claim 2, wherein the diacid is terephthalic acid.

9. The process of claim 1, wherein the acid hydrogenation catalyst comprises (a) a ruthenium compound; and (b) a tridentate triphosphine compound selected from 1,1,1-tris(diarylphosphinomethyl)alkyl in which the alkyl is substituted or unsubstituted.

10. The process of claim 9, wherein the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes, and combinations of two or more of the foregoing; and the tridentate triphosphine compound is selected from tris(diphenylphosphinomethyl)alkyl or substituted alkyl.

11. The process of claim 9, wherein the ruthenium compound and the tridentate triphosphine compound are the same compound.

12. The process of claim 9, wherein the tridentate triphosphine compound comprises 1,1,1-tris(diphenylphosphinomethyl)ethane.

13. The process of claim 9, wherein the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes, and combinations of two or more of the foregoing; and the tridentate triphosphine compound is selected from tris(diphenylphosphinomethyl)alkyl or substituted alkyl.

14. The process of claim 9, wherein the process further comprises feeding to the second reaction zone a promoter selected from Lewis acids, protic acids having an ionization constant ($K_i$) of $5 \times 10^{-3}$ or greater, onium salts, and combinations of two or more of the foregoing.

15. The process of claim 14, wherein the promoter is selected from ammonium hexafluorophosphate, tetrabutylammonium hexafluorophosphate, tetraphenylphosphonium bromide, sodium tetraphenyl borate, ammonium tetrafluoroborate, tetramethyl ammonium tetrafluoroborate, toluenesulfonic acid, phosphoric acid, triflic acid, sulfuric acid, methanesulfonic acid, trifluoroacetic acid, dodecylbenzenesulfonic acid, dinonylnaphthalenesulfonic acid, and combinations of two or more of the foregoing.

16. The process of claim 14, wherein the promoter is selected from tetrabutylammonium hexafluorophosphate, triflic acid, toluenesulfonic acid, dodecylbenzenesulfonic acid, dinonylnaphthalenesulfonic acid, and combinations of two or more of the foregoing.

17. The process of claim 1, wherein the reaction zone has a pressure of from about 500 to about 3,000 psig and a temperature of from about 100 to about 240° C.

18. The process of claim 1, further comprising processing at least some of the product composition in a first separation zone to remove at least some of the acid hydrogenation catalyst from the product composition.

19. The process of claim 1, further comprising processing at least some of the product composition in a second separation zone to concentrate the hydroxymethylbenzoic acid in a crude product stream and to concentrate the solvent compound in a recovered solvent stream.

20. The process of claim 19, wherein the process further comprising recycling at least some of the recovered solvent stream to the reaction zone.

* * * * *